United States Patent
Kositprapa et al.

(10) Patent No.: US 8,529,946 B2
(45) Date of Patent: Sep. 10, 2013

(54) RAPIDLY DISINTEGRATING ANTIHISTAMINE FORMULATION

(75) Inventors: Unchalee Kositprapa, Davie, FL (US); Nilobon Podhipleux, Weston, FL (US); Avinash Nangia, Weston, FL (US); Samuel Yuk, Boca Raton, FL (US)

(73) Assignee: Andrx Pharmaceuticals, LLC, Davie, FL (US)

( * ) Notice: Subject to any disclaimer, the term of this patent is extended or adjusted under 35 U.S.C. 154(b) by 2144 days.

(21) Appl. No.: 10/951,737

(22) Filed: Sep. 28, 2004

(65) Prior Publication Data

US 2005/0042286 A1    Feb. 24, 2005

Related U.S. Application Data

(63) Continuation of application No. 10/183,771, filed on Jun. 27, 2002, now abandoned.

(51) Int. Cl.
    *A61K 9/20*      (2006.01)

(52) U.S. Cl.
    USPC ........................................................ 424/464

(58) Field of Classification Search
    None
    See application file for complete search history.

(56) References Cited

U.S. PATENT DOCUMENTS

| | | |
|---|---|---|
| 4,134,943 A | 1/1979 | Knitsch et al. |
| 4,282,233 A | 8/1981 | Vilani |
| 4,371,516 A | 2/1983 | Gregory et al. |
| 4,659,716 A | 4/1987 | Villani et al. |
| 4,996,061 A | 2/1991 | Webb et al. |
| 5,178,878 A | 1/1993 | Wehling et al. |
| 5,298,261 A | 3/1994 | Pebley et al. |
| 5,503,846 A * | 4/1996 | Wehling et al. ............ 424/466 |
| 5,587,180 A | 12/1996 | Allen, Jr. et al. |
| 5,691,370 A | 11/1997 | Cupps et al. |
| 5,720,974 A | 2/1998 | Makino et al. |
| 5,738,875 A | 4/1998 | Yarwood et al. |
| 5,741,524 A | 4/1998 | Staniforth et al. |
| 5,807,576 A | 9/1998 | Allen, Jr. et al. |
| 5,837,287 A | 11/1998 | Yarwood et al. |
| 5,866,163 A * | 2/1999 | Myers et al. ............... 424/469 |
| 5,869,098 A | 2/1999 | Misra et al. |
| 5,869,479 A | 2/1999 | Kreutner et al. |
| 6,010,719 A | 1/2000 | Remon et al. |
| 6,024,981 A * | 2/2000 | Khankari et al. ........... 424/464 |
| 6,027,746 A * | 2/2000 | Lech ........................... 424/455 |
| 6,048,541 A | 4/2000 | Misra et al. |
| 6,156,339 A | 12/2000 | Grother et al. |
| 6,177,104 B1 | 1/2001 | Allen et al. |
| 6,207,199 B1 | 3/2001 | Allen et al. |
| 2002/0086059 A1 | 7/2002 | Bausch et al. |
| 2002/0119196 A1* | 8/2002 | Parikh et al. ............... 424/472 |

OTHER PUBLICATIONS

Physician's Desk Reference, p. 2613-2615, (52nd Edition 1998).

* cited by examiner

*Primary Examiner* — Brian Gulledge
*Assistant Examiner* — Snigdha Maewall
(74) *Attorney, Agent, or Firm* — Florek & Endres PLLC

(57) ABSTRACT

The invention relates to a rapidly disintegrating oral antihistamine dosage formulation and method of preparing the rapidly disintegrating formulation wherein the formulation is designed to dissolve in the buccal cavity of the patient.

6 Claims, No Drawings

RAPIDLY DISINTEGRATING ANTIHISTAMINE FORMULATION

The present application is a continuation of U.S. patent application Ser. No. 10/183,771 filed on Jun. 27, 2002 now abandoned.

FIELD OF THE INVENTION

The present invention relates to the field of oral dosage forms and in particular the field of rapidly disintegrating oral dosage formulations that disintegrate rapidly in the saliva of the buccal cavity and can be swallowed easily with or without drinking water. As used in this application the term "rapidly disintegrating" means that the dosage formulation dissolves in an aqueous media within 5 minutes, preferably less than two minutes and most preferably less than one minute.

BACKGROUND OF THE INVENTION

Antihistamines are a well known class of pharmaceutically active compounds, some of which are described in U.S. Pat. Nos. 5,869,479, 5,691,370 and Remington's 20$^{th}$ Ed., pages 1464-1470 which are incorporated herein by reference.

Piperidinoalkanol derivatives which are disclosed in U.S. Pat. No. 4,996,061 and incorporated herein by reference are a particular class of antihistamine. Loratadine is a specific type of piperidinoalkanol and is disclosed in U.S. Pat. No. 4,282,233 as an antihistamine with little or no sedative effect. Schering Corporation currently markets a rapidly disintegrating form of loratadine under the tradename CLARITIN REDITABS. CLARITIN REDITABS contain 10 mg of micronized loratadine and disintegrate in the mouth within seconds after placement on the tongue, allowing its contents to be subsequently swallowed with or without water. CLARITIN REDITABS also contain citric acid, gelatin, mannitol and mint flavoring. See Physicians' Desk Reference, 52$^{nd}$ Ed., pp. 2613-2615.

Another antihistamine is the active metabolite of loratadine, known as descarboethoxyloratadine. Descarboethoxyloratadine is disclosed in U.S. Pat. No. 4,659,716 and is prepared by the removal of the carboethoxy moiety from the loratadine molecule. Still other antihistamines that are known and can be used in the present invention are astemizole, azatadine, cetirizine, fexofenadine and pharmaceutically acceptable salts of these compounds.

Rapidly disintegrating dosage formulations are known in the art. Some rapidly disintegrating dosage formulations are described in U.S. Pat. Nos. 4,371,516; 5,298,261; 5,587,180; 5,720,974; 5,807,576; 5,866,163; 5,869,098 and 6,048,541 which are incorporated herein by reference. The prior art rapidly disintegrating formulations require complicated processing techniques such as lyophilazation foam techniques or specialized excipients.

It is therefore an objective of the present invention to provide a safe and effective rapidly disintegrating oral antihistamine dosage formulation that can be economically be prepared.

SUMMARY OF THE INVENTION

In the present invention, the filler is a mixture of water soluble and water insoluble fillers.

The rapidly disintegrating oral dosage formulation of the present invention may also contain conventional processing aids such as solubilizers, glidants and lubricants. These conventional processing aids are well know to the skilled artisan and are used in amounts that do not materially affect the final properties of the dosage formulation.

The rapidly disintegrating oral dosage formulation of the present invention can be prepared by any of the conventional processing techniques known in the art, however, the preferred method involves granulation and tableting of the granules. The most preferred method involves: a) preparing a wet granulation of the antihistamine, binder and 40-70 weight percent of filler based upon the total weight of the filler employed in the final dosage formulation; b) blending the antihistamine granules from step (a) with the disintegrant, taste enhancing agent and 30-60 weight percent of filler based upon the total weight of the filler employed in the final dosage formulation; and c) compressing the blend of step (b) into a tablet. If a mixture of water soluble and water insoluble filler is employed in the dosage formulation, 75-100 percent, preferably 100% of the water insoluble filler, should be used in preparation of the antihistamine granules.

DETAILED DESCRIPTION OF THE INVENTION

The rapidly disintegrating oral dosage formulation of the present invention may comprise the following ingredients:

| INGREDIENT | PREFERRED | MOST PREFERRED |
|---|---|---|
| ANTIHISTAMINE | 5-40% | 5-20% |
| FILLER | 40-90% | 60-85% |
| BINDER | 0.5-10% | 1-5% |
| TASTE ENHANCING AGENT | 0.5-10% | 1-7% |
| DISINTEGRANT | 1-15% | 2.5-10% |

All the percentages in the above table are based on the total weight of the dosage formulation.

Any antihistamine can be used in the present invention. Preferred antihistamines are astemizole, azatadine, cetirizine, descarboethoxyloratadine, fexofenadine, loratadine or a pharmaceutically acceptable salt thereof. The term "pharmacologically acceptable salts" encompasses both organic and inorganic salts including, for example sodium, hydrochloric, hydrofluoric, sulfuric, sulfonic, tartic, fumaric, hydrobromic, glycolic, citric, maleic, sulfate, phosphoric, succinic, acetic, nitric, benzoic, ascorbic, p-toluene sulfonic, benzenesulfonic, naphthalenesulfonic, propionic, and the like.

The filler used in the formulation may be any pharmaceutically acceptable filler. Some of the preferred fillers are lactose, starch, dextrose, sucrose, fructose, maltose, mannitol, sorbitol, kaolin, microcrystalline cellulose, powdered cellulose or any combination of the foregoing. In a preferred embodiment of the present invention, the filler consists of a mixture of water soluble and water insoluble fillers. Preferably the amount of the water soluble filler should be at least 50 weight percent based upon the total weight of the filler, preferably at least 60 weight percent based on the total weight of the filler and most preferably at least 70 weight percent based on the total weight of the filler.

The binder may be any pharmaceutically acceptable binder. The binder is preferably a water soluble polymer of the group consisting of polyvinyl alcohol, polyvinylpyrrolidone, methylcellulose, hydroxypropyl cellulose, hydroxymethyl cellulose and any combination of the foregoing. Polyvinylpyrrolidone is the most preferred binder.

The disintegrant used in the present invention can be selected from the group consisting of corn starch, croscarmelose sodium, crospovidone (polyplasdone XL-10, sodium starch glycolate (EXPLOTAB or PRIMOJEL) or any combination of the foregoing. The most preferred disintegrant is crospovidone or sodium starch glycolate.

The flavoring agent preferably are taste enhancing agents and can include artificial sweeteners such as aspartame, saccharin, dipotassium glycyrrhizinate, stevia, thaumatin and flavorants such as citric acid, peppermint oil, wintergreen oil, menthol, lemon, lime, orange grape, cherry and vanilla extract. Additional taste enhancing agents are described in U.S. Pat. No. 6,027,746 and are incorporated herein by reference. In a preferred embodiment of the present invention, the flavoring agent is preferably a taste enhancing agent and may comprise a mixture of artificial sweeteners and flavorants.

The present invention may also comprise conventional processing aids such as tablet lubricants (magnesium stearate, sodium stearate), glidants (colloidal silicon dioxide) and wetting agents or solubilizers (sodium lauryl sulfate, polysorbates). The processing aids are generally added to the dosage formulation in small amounts (less than 2 weight percent) and do not materially affect the properties of the final dosage formulation.

The following example illustrates the present invention and is not intended to limit the scope of the present invention.

EXAMPLE 1

An antihistamine tablet containing loratadine is prepared according to the following procedure:

Stage I Homogenation 0.333 kg of Povidone K-30 is added to purified water while homogenizing with a homogenizer for 5 minutes at a speed greater than about 1,200 r.p.m. to form a solution.

0.033 kg of sodium lauryl sulfate is added to the solution. The homogenizer speed is reduced to below 800 r.p.m. in order to prevent excess foaming and homogenization is continued for about 2 minutes.

3.333 kg of micronized loratadine is slowly added to the solution and homogenized until the loratadine is completely dispersed.

The homogenizer is rinsed and replaced with a mechanical stirrer and the suspension is stirred continually throughout the entire process.

Stage II 1.633 kg of Mannitol and 4.667 kg of microcrystalline cellulose (Avicel™ PH101) are loaded onto a fluidized bed coater and the drug suspension is sprayed onto the substrates. The inlet air temperature is between 30 and 60° C., outlet air temperature is between 20 and 45° C., atomization pressure is between 0.8-3.5 bar, and the pump rate is about 20-120 ml/minute.

After the suspension is consumed, the pump is stopped and the granules are dried in the fluidized bed coater for 20 minutes at 30-40° C. product temperature. If the amount of loss on drying is greater than 2.5% then the granules are placed in an oven.

The granules are then placed through a co-mil equipped with a #1143 screen and a 0.175" spacer at 800 to 1500 r.p.m. and collected.

Stage III Blending

The following materials as shown in TABLE I as blended for 10 minutes at 32 r.p.m.

TABLE I

| | |
|---|---|
| D-Mannitol | 1.865 kg |
| Colloidal silicon dioxide (Cab-O-Sil) | 0.240 kg |

TABLE I-continued

| | |
|---|---|
| Citric Acid | 0.088 kg |
| Aspartame | 0.188 kg |
| Artificial Cherry Flavor | 0.118 kg |
| Crospovidone (Polyplasdone) | 0.588 kg |
| Lactose, monohydrate | 3.5 kg |

The blended mixture is passed through a comil equipped with a #1143 sized stainless steel screen with a 0.175 spacer at 1200-1800 r.p.m. forming a powder blend.

The loratadine granules from STAGE II and the powder blend from STAGE III are blended for 10 minutes at 32 rpm.

Sodium stearate is passed through a 30 mesh screen and blended for 10 minutes at 32 r.p.m. Unit dose samples are then collected in separate containers.

Stage IV Compression

The blend is then compressed into tablets on a tablet press using a ¼ inch round flat-faced beveled-edge die. The tablet hardness should range between 0.5 and 2.0 kp, and preferably around 0.75 to 1.5, most preferably about 1.21 kp, measured by techniques commonly used in the art.

The dosage form described herein can be used to provide fast relief from colds, Flu, allergies, and other respiratory diseases. In order to achieve fast release, the tablet is placed inside the mouth of the patient. The tablet will rapidly disintegrate upon contact with any aqueous media. In the mouth, the disintegrated tablet is carried to the stomach where the drug is absorbed and utilized by the patient to provide antihistamine therapy.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

We claim:

1. A method for manufacturing an oral antihistamine tablet consisting of:
   a) 5-20 weight percent of loratadine or descarboethoxyloratadine;
   b) 60-86 weight percent of a filler;
   c) 1-5 weight percent of a water soluble polymeric binder;
   d) 1-7 weight percent of a taste enhancing agent;
   e) 2.5-10 weight percent of a disintegrant; and
   f) sodium stearate,
   wherein the method consists of the following steps:
   i) wet granulating with water:
      A) the loratadine or descarboethoxyloratadine;
      B) 40-70 weight percent of a first allotment of the filler based upon the total weight of the filler employed in the tablet wherein the first allotment of filler consists of mannitol and microcrystalline cellulose; and
      C) the water soluble polymeric binder;
   ii) drying and screening the granules formed in step (i);
   iii) blending the granules from step (i) with:
      (A) the disintegrant;
      (B) 30-60 weight percent of a second allotment of filler based upon the total weight of the filler employed in the tablet wherein the filler is selected from the group consisting of lactose, mannitol and combinations of the foregoing;
      (C) the taste enhancing agent; and
      (D) sodium stearate, and iv) compressing the blend of step (iii) into a tablet with a hardness between 0.75 and 1.5 kp and wherein the tablet dissolves in an aqueous media within 5 minutes and disintegrates when placed in a buccal cavity of a patient to enable swallowing with or without water.

2. The method recited in claim 1 wherein the tablet dissolves in an aqueous media in less than 1 minute.

3. The method recited in claim 1 wherein the tablet dissolves in an aqueous media in less than 2 minutes.

4. A tablet prepared according to the method of claim 1.

5. A tablet prepared according to the method of claim 3.

6. A tablet prepared according to the method of claim 2.

* * * * *